United States Patent
Wade

(10) Patent No.: US 12,350,113 B2
(45) Date of Patent: *Jul. 8, 2025

(54) SYSTEM AND METHOD FOR ENHANCED DATA ANALYSIS WITH SPECIALIZED VIDEO ENABLED SOFTWARE TOOLS FOR MEDICAL ENVIRONMENTS

(71) Applicant: Jack Wade, La Jolla, CA (US)

(72) Inventor: Jack Wade, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/231,782

(22) Filed: Aug. 8, 2023

(65) Prior Publication Data

US 2024/0033034 A1 Feb. 1, 2024

Related U.S. Application Data

(63) Continuation of application No. 17/341,225, filed on Jun. 7, 2021, now Pat. No. 11,744,668, which is a
(Continued)

(51) Int. Cl.
*A61B 90/00* (2016.01)
*A61B 1/00* (2006.01)
(Continued)

(52) U.S. Cl.
CPC ........ *A61B 90/361* (2016.02); *A61B 1/00009* (2013.01); *A61B 1/000095* (2022.02); *A61B 1/00011* (2013.01); *A61B 1/0005* (2013.01); *A61B 1/3132* (2013.01); *A61B 5/0084* (2013.01); *A61B 5/0095* (2013.01); *A61B 5/1032* (2013.01); *A61B 34/25* (2016.02);
(Continued)

(58) Field of Classification Search
None
See application file for complete search history.

(56) References Cited

U.S. PATENT DOCUMENTS

| | | | |
|---|---|---|---|
| 6,271,752 B1 * | 8/2001 | Vaios | H04N 7/141 348/E7.086 |
| 6,285,902 B1 * | 9/2001 | Kienzle, III | A61B 17/1721 378/205 |

(Continued)

*Primary Examiner* — Nancy Bitar
(74) *Attorney, Agent, or Firm* — Olivo IP Law Group, P.C.; John W. Olivo, Jr.

(57) ABSTRACT

Medical software tools platforms utilize a surgical display to provide access to specific medical software tools, such as medically-oriented applications or widgets, that can assist surgeons or surgical team in performing various procedures. In particular, an endoscopic camera may register the momentary rise in the optical signature reflected from a tissue surface and in turn transmit it to a medical image processing system which can also receive patient heart rate data and display relevant anomalies. Changes in various spectral components and the speed at which they change in relation to a source of stimulus (heartbeat, breathing, light source modulation, etc.) may indicate the arrival of blood, contrast agents or oxygen absorption. Combinations of these may indicate various states of differing disease or margins of tumors, and so forth. Also, changes in temperatures, physical dimensions, pressures, photoacoustic pressures and the rate of change may indicate tissue anomalies in comparison to historic values.

19 Claims, 11 Drawing Sheets

Related U.S. Application Data continuation of application No. 16/677,590, filed on Nov. 7, 2019, now Pat. No. 11,051,903, which is a continuation of application No. 15/958,983, filed on Apr. 20, 2018, now Pat. No. 10,507,075, which is a continuation-in-part of application No. 15/789,948, filed on Oct. 20, 2017, now abandoned, which is a continuation-in-part of application No. 15/652,031, filed on Jul. 17, 2017, now Pat. No. 10,433,917, which is a continuation-in-part of application No. 15/456,458, filed on Mar. 10, 2017, now Pat. No. 10,758,314, which is a continuation-in-part of application No. 15/377,817, filed on Dec. 13, 2016, now abandoned, said application No. 16/677,590 is a continuation-in-part of application No. 15/170,575, filed on Jun. 1, 2016, now Pat. No. 10,142,641, said application No. 15/377,817 is a continuation of application No. 14/107,329, filed on Dec. 16, 2013, now Pat. No. 9,526,586, said application No. 15/170,575 is a continuation of application No. 13/430,489, filed on Mar. 26, 2012, now abandoned, which is a continuation-in-part of application No. 12/776,048, filed on May 7, 2010, now Pat. No. 8,266,333.

(60) Provisional application No. 61/865,037, filed on Aug. 12, 2013, provisional application No. 61/234,577, filed on Aug. 17, 2009, provisional application No. 61/182,624, filed on May 29, 2009.

(51) Int. Cl.
| | | |
|---|---|---|
| *A61B 1/313* | (2006.01) | |
| *A61B 5/00* | (2006.01) | |
| *A61B 5/024* | (2006.01) | |
| *A61B 5/103* | (2006.01) | |
| *A61B 34/00* | (2016.01) | |
| *A61B 90/30* | (2016.01) | |
| *G06F 3/0481* | (2022.01) | |
| *G16H 10/00* | (2018.01) | |
| *G16H 10/60* | (2018.01) | |
| *G16H 20/40* | (2018.01) | |
| *G16H 30/40* | (2018.01) | |
| *G16H 40/63* | (2018.01) | |
| *G16H 40/67* | (2018.01) | |
| *G16H 50/20* | (2018.01) | |
| *G16H 50/70* | (2018.01) | |
| *H04L 67/125* | (2022.01) | |
| *H04N 7/14* | (2006.01) | |
| *H04N 7/18* | (2006.01) | |

(52) U.S. Cl.
CPC .......... *G06F 3/0481* (2013.01); *G16H 10/00* (2018.01); *G16H 10/60* (2018.01); *G16H 20/40* (2018.01); *G16H 30/40* (2018.01); *G16H 40/63* (2018.01); *G16H 40/67* (2018.01); *G16H 50/20* (2018.01); *G16H 50/70* (2018.01); *H04N 7/147* (2013.01); *A61B 5/0075* (2013.01); *A61B 5/024* (2013.01); *A61B 90/30* (2016.02); *A61B 2090/3612* (2016.02); *G06T 2200/24* (2013.01); *G06T 2207/30004* (2013.01); *H04L 67/125* (2013.01); *H04N 7/183* (2013.01)

(56) References Cited

U.S. PATENT DOCUMENTS

| | | | | |
|---|---|---|---|---|
| 7,039,723 | B2* | 5/2006 | Hu | G16H 30/20 |
| | | | | 709/248 |
| 8,295,649 | B2* | 10/2012 | Berini | G06V 10/94 |
| | | | | 382/304 |
| 2003/0051021 | A1* | 3/2003 | Hirschfeld | H04L 67/1027 |
| | | | | 709/223 |
| 2003/0104806 | A1* | 6/2003 | Ruef | H04M 3/42 |
| | | | | 348/E7.079 |
| 2003/0159141 | A1* | 8/2003 | Zacharias | H04N 5/445 |
| | | | | 348/E5.093 |
| 2008/0071144 | A1* | 3/2008 | Fein | A61B 1/07 |
| | | | | 600/178 |
| 2012/0330103 | A1* | 12/2012 | Tenger | A61M 16/0429 |
| | | | | 600/188 |
| 2014/0171759 | A1* | 6/2014 | White | A61B 5/6835 |
| | | | | 600/306 |
| 2015/0282749 | A1* | 10/2015 | Zand | A61B 1/0676 |
| | | | | 600/301 |
| 2016/0166336 | A1* | 6/2016 | Razzaque | A61B 90/37 |
| | | | | 606/130 |
| 2019/0133711 | A1* | 5/2019 | Wade | G16H 30/40 |

* cited by examiner

SYSTEM AND METHOD FOR ENHANCED DATA ANALYSIS WITH SPECIALIZED VIDEO ENABLED SOFTWARE TOOLS FOR MEDICAL ENVIRONMENTS

PRIORITY CLAIMS

This application is a continuation of U.S. patent application Ser. No. 17/341,225, filed Jun. 7, 2021, which is a continuation of U.S. patent application Ser. No. 16/677,590, filed Nov. 7, 2019, which is a continuation of U.S. patent application Ser. No. 15/958,983, filed Apr. 20, 2018, and issued as U.S. Pat. No. 10,507,075 on Dec. 17, 2019, which is a continuation in part of U.S. patent application Ser. No. 15/789,948, filed Oct. 20, 2017, which is a continuation in part of U.S. patent application Ser. No. 15/652,031, filed Jul. 17, 2017, issued as U.S. Pat. No. 10,433,917, on Oct. 8, 2019, which is a continuation in part of U.S. patent application Ser. No. 15/456,458, filed Mar. 10 2017, which is a continuation in part of U.S. patent application Ser. No. 15/377,817, filed Dec. 13, 2016, which is a continuation of U.S. patent application Ser. No. 14/107,329, filed Dec. 16, 2013, and issued as U.S. Pat. No. 9,526,586 on Dec. 27, 2016, which claims the benefit of U.S. Provisional Patent Application Ser. No. 61/865,037, filed Aug. 12, 2013. This application also claims the benefit of and is a continuation in part of U.S. patent application Ser. No. 15/170,575, filed Jun. 1, 2016, issued as U.S. Pat. No. 10,142,641, on Nov. 27, 2018, which is a continuation of U.S. patent application Ser. No. 13/430,489, filed Mar. 26, 2012, which is a continuation-in-part of U.S. patent application Ser. No. 12/776,048, filed May 7, 2010, and issued as U.S. Pat. No. 8,266,333, on Sep. 11, 2012, which claims the benefit of U.S. Provisional Patent Application Ser. No. 61/182,624, filed May 29, 2009, and Ser. No. 61/234,577, filed Aug. 17, 2009. Each of the foregoing applications is hereby incorporated by reference.

TECHNICAL FIELD

The technology disclosed herein relates to medical software tools and, in particular, some embodiments relate to systems and methods for a software tools platform in a medical environment, such as a surgical environment, incorporating enhanced data analysis.

BACKGROUND OF THE INVENTION

During minimally invasive surgeries, medical imaging devices may be introduced into a subject's body to illuminate and image body cavities, organs or other tissue. Advantages of using internal medical imaging devices include the ability to avoid large incisions and the ability to image biological tissue. Many imaging devices also include one or more lenses that focus images onto an eyepiece and/or imaging lens. Still or video cameras may be used to capture image data using a medical imaging device.

Medical imaging devices can enable surgeries to be performed in a manner that is less intrusive and often safer for patients. While this brings many benefits to patients, it presents a number of challenges for the surgeon who must work within a very confined surgical compartment. In particular, surgeons must deal with poor visibility, limited lighting, and a narrow viewing angle. Because of their size, conventional medical imaging devices tend to have limited imaging resolution, often fail to provide more than one perspective of biological tissue, and due to visible lighting constraints, often fail to show differences in biological tissue.

Minimally invasive surgeries increasingly occur in operating rooms equipped with advanced audio-visual technology. At one end of the spectrum are integrated operating rooms, that combine high resolution video displays, touch screen control, access to digital information through the hospital network, and data archiving capability into an interconnected purpose-built system. In addition to facilitating surgical procedures and improving efficiency, integrated operating rooms can also connect the surgeon in the sterile field with people and information outside the operating room. For example, an integrated operating room can enable: live consultation with pathology and ICU; real-time collaboration with surgeons across the globe; live feeds to conference rooms and auditoriums for training and grand rounds; and data exchange with an electronic medical record system, radiological picture archiving and communication system (PACS), or network-enabled devices in other operating and treatment rooms.

In many surgical procedures it is critical to monitor the status or health of tissue or organs surrounding any given surgical procedure. Perfusion, which measures the rate tissue or an organ absorbs fluid, can be used to distinguish normal tissue from diseased tissue. One technique used is to inject contrast fluid into the blood stream and use imaging modalities to measure the rate the blood spreads through the tissue or organ. Another technique is to use an endoscopic optical sensor to measure both the amount and speed of change in one or more of the spectral components reflected from the surface of tissue or an organ in response to a heartbeat, a patient's breath, or an external stimulus to measure and characterize the state of body tissue and organs.

SUMMARY OF THE INVENTION

Various embodiments of the disclosed technology provide a medical software tools platform that utilizes a surgical display to provide access to medical software tools, such as medically-oriented applications or widgets, that can assist those in the operating room, such as a surgeon and their surgical team, with a surgery. For various embodiments, the medical. software tools platform and its associated medical software tools are presented on a surgical display (e.g., being utilized in an operating room) over an image stream provided by a surgical camera (e.g., in use in the operating room) or other medical device that generates image streams. An image stream can include video or a series of static images (e.g., medical ultrasound device). Various medical software tools can provide features and functions that can facilitate integration of equipment in an operating room or add medical context awareness to anatomic structures presented in the image stream from the surgical camera.

Medical video display panels and multiscreen displays are commonly employed in such contexts as hospital operating theaters or any facility where surgical operations are carried out in a sterile environment. They are used to display visual information from data streams such as surgical imagery from an endoscope, patient vital signs, patient medical records, clinical imaging data (patient CT scans, MRIs, etc.), outputs from other operating room equipment, and operating room environmental status. Surgical displays and multiscreen video displays provide a surgeon and their surgical team with visual information that can be automatically updated, or can be used to enable collaboration among viewers. Where a surgical display or multiscreen video display is used for group collaboration, there is generally a requirement that the group has the ability to update and reconfigure the visual information displayed, which is usually facilitated through a video switch. Traditional video switches are controlled through a switch box, a keyboard, or a local connection (via an RS-232 port or Ethernet port) and have only a single point for control access. In some contexts, visual data streams to a single large panel video display or a multiscreen display configuration are provided by two or more computer systems, each being controlled by a computer operator (i.e., user) using such input/output (TO) devices as keyboards, mice, and as video monitor. At times, it is convenient for the computer operator to share the IO devices between the computers by means of a device that switches the IO devices between the multiple computers. These switches, often referred to as a Keyboard-Video-Mouse (KVM) switch, are commanded by the computer operator (e.g., commanded by a special keyboard sequence or a button on the KVM switch) to switch a common keyboard, mouse, or video monitor between controlling the computer systems.

According to some embodiments, a system comprises an image stream interface module configured to receive an image stream from a surgical camera, a user interface overlay module configured to provide a user interface overlay adapted for presentation over the image stream, and a medical software tools module configured to provide a medical software tool through the user interface overlay. The medical software tool may be configured to perform an operation with respect to the image stream and provide an output adapted to be presented over the image stream. The user interface overlay can include a graphical user interface (GUI) that permits visibility of at least some of the image stream underlying the user interface overlay. The user interface overlay module is further configured to present the output over the image stream. Depending on the embodiment, the surgical camera may be an endoscope or a laparoscope. Additionally, the image stream interface module may receive the image stream from the surgical camera through an image stream processing system.

Throughout this description, a user interface will be understood to be accessible to any user involved in a medical procedure, such as a surgery. It will also be understood that a user can include any individual involved in a given medical procedure, such as a nurse or a surgeon.

In some embodiments, the system comprises a medical device communication module configured to exchange data between a medical device and the medical software tool. Through the medical device interface module, some embodiments can enable a medical software tool to present information from disparate medical devices, or facilitate sharing of information between medical devices. In some embodiments, the system comprises an image stream processing system interface module configured to exchange data between an image stream processing system and the medical software tool, the medical software tool being configured to modify a setting of the image stream processing system. The setting of the image stream processing system can include enabling or disabling application of an image stream processing algorithm to the image stream. Through the image stream processing system interface module, the medical software tool can control how the image stream processing system receives and processes image streams eventually presented on the surgical display.

Depending on the embodiment, the operation performed by the medical software tool may comprise a visual tag over the image stream in association with an anatomical structure or tissue presented in the image stream, and the output may comprise the visual tag. The operation performed by the medical software tool may comprise measuring an anatomical structure or tissue (e.g., width, height, length, or volume) presented in the image stream, and the output may comprise a resulting measurement. Where the image stream comprises two-dimensional content, the operation may comprise converting at least some of the two-dimensional content into three-dimensional content, and the output may comprise the three-dimensional content (e.g., stereoscopic three-dimensional content). The operation performed by the medical software tool may comprise associating content in the image stream with a timer, and the output may comprise a visual representation of the timer. The operation performed by the medical software tool may comprise identifying content (e.g., anatomic structure) in the image stream similar to reference content (e.g., reference anatomic structure), and the output may comprise a visual indication of the identified content. The operation performed by the medical software tool may comprise aiding the surgeon in identifying anomalous tissue or defining the margins of a tumor or diseased area to be excised by analyzing subtle color changes in the tissue called micro-blushes, caused by the blood rushing in and out, to create an optical signature.

A system or method in accordance with the present invention may selectively and dynamically route one or more image input streams through one or more dynamically selectable and iterative algorithm processing elements (or modules) before the resulting processed streams are routed to one or more selectable outputs. For some embodiments, dynamic selection with respect to inputs means that one or more inputs can be selected or unselected in real time for routing to one or more image processing elements. For additional embodiments, dynamic and iterative selection with respect to processing elements means that a selected image stream can be routed to one or more image processing elements simultaneously and in real time. The routing may be based upon criteria relating to the image stream's source, the image stream's content, or on the processing results of a preceding image processing element. The output of an image processing element may be directed back to the system or method for routing to a subsequent image processing element, or to one or more image outputs that supply an image stream to an output device (e.g., display, image recorder, or other image processor, or transmission device).

An exemplary system for collaboratively switching an image stream input to an image stream output, comprising: an image stream input interface; an image stream output interface; a first image processing module, wherein the first image processing module is configured to accept an image stream from the image stream input interface or another image processing module, apply an image processing function to the image stream, and output a processed image stream; and a switching matrix, wherein the switching matrix is in communication with the image stream input interface, the image stream output interface, and the first image processing module such that the switching matrix can selectively map (i.e., route) the image stream input interface to the image stream output interface or to the first image processing module, and the switching matrix can selectively map the processed image stream from the first image processing module to the image stream output interface or to a second image processing module. An image stream includes both a steady flow of image frames (i.e., video) and image stills captured at a set interval (e.g., once every hour). Additionally, for some embodiments the system comprises a plurality of image processing modules, a plurality of image stream input interfaces, or a plurality of image stream output interfaces. Furthermore, in further embodiments, the system may be integrated into a display having a display output, wherein the image stream output interface is in communication with the display output.

In some embodiments, the image processing module is a field programmable gate array (FPGA) to which algorithms, such as image processing functions, can be programmed and changed if desired. Additionally, with the use of multiple images processing functions, algorithms, such as image processing functions, can be executed in a predetermined or adaptive sequence. Exemplary algorithms include convolutions, real-time adaptive histograms, and algorithms capable of processing multiple frames simultaneously (e.g., image subtraction function).

One of ordinary skill in the art would understand that, depending on the embodiment, either the image stream input interface, the image stream output interface, or both may utilize unidirectional communication or bidirectional communication with input devices and output devices. For example, a system may be configured to receive control information from a controller interface device via an image stream output interface, or to send control information to an image source via an image stream input interface. In another example, the control information is received by the system through the Display Data Channel (DDC). Depending on the embodiment, the system may be configured to send control information to a device external to the system, through the image stream input interface.

In some embodiments, the switching matrix may selectively map an image stream input interface or a processed image stream in real-time. In further embodiments, the switching matrix may selectively map the image stream input interface to more than one image processing module or to more than one image stream output interface simultaneously. Additionally, in some embodiments, the switching matrix may selectively map the processed image stream to more than one image processing module or to more than one image stream output interface simultaneously. In other embodiments, the switching matrix may selectively map an image stream input interface or the processed image stream based on a criterion. For example, the switching matrix may selectively map an image stream input interface or a processed image stream based on its source or content. In another example, the switching matrix may selectively map a processed image stream based on the results of a preceding image processing module. Depending on the embodiment, the image processing module may have the capability of processing a plurality of image streams in parallel. The image stream interface for some embodiments may be configured to receive the image stream from an image stream capture device, an image stream playback device, a computer system, a sensor device or a medical device (e.g., endoscope). The image stream output interface for some embodiments may be configured to output to a display (e.g., liquid crystal display monitor), a computer system, or recording device (e.g., digital video recorder). Further, in some embodiments, the system may be configured to output an image stream through a virtual display.

In numerous embodiments, the system further comprises a data input interface, wherein the switching matrix is further in communication with the data input interface such that the switching matrix can further selectively map the data input interface to the image stream output interface or to the first image processing module. For some such embodiments, the image stream input interface may comprise the data input interface.

With respect to protocols and interface types, in various embodiments, the image stream input interface or image stream output interface has a Digital Video Interface (DVI) connector, High-definition Multimedia Interface (HDMI) connector, a Bayonet Neill-Concelman (BNC) connector, a fiber optic connector, a DisplayPort connector, a Universal Serial Bus (USB) connector, or a Fire wire (IEEE1394) connector. In regard to formats, the image stream input interface is configured to convert from or the image stream output interface is configured to: a Digital Video Interface (DVI) standard (e.g., DVI-D digital mode, DVI-A analog mode), a High-definition Multimedia Interface (HDMI) compatible standard, a Red-Green-Blue (RGB) Analog standard, a Red-Green-Blue (RGB) Digital standard, a DisplayPort standard, a National Television System Committee (NTSC) standard, a Phase Alternate Line (PAL) standard, or a Serial Digital Interface (SDI) standard.

The image processing function in some embodiments may comprise an image stream mix function, an image stream scale function, an image stream blend function, an image stream encoding algorithm, or an image stream enhancement function. For those embodiments having an image stream enhancement function, the image stream enhancement function may comprise a de-haze function, a de-blur function, a shadow function, a dawn-dusk function, a fusion function, a (motion) stabilization function, a thermal turbulence function, an equalization function, an edge detection function, a rain and fog function, or a light optimizing function. Further, in some embodiments, the system can eliminate or reduce frame latency by configuring an image processing module to apply processing results of a given frame to a subsequent frame.

In additional embodiments, where the image stream is provided by an endoscope, the image processing function can enhance the image stream for detecting texture differences in living tissue, detecting a polyp, detecting anomalous tissue, detecting blood circulation, or identifying reference locations for subsequent registration of images from another modality. In further embodiments, a light optimizing function may adjust a color channel for the image stream in order to detect polyps. For example, the system may apply image processing functions in real time to image feeds from an endoscope in order to detect differences in living tissue, detect anomalous tissue, determine boundaries where tissue texture changes (for tissue volume and size information), and identify reference locations for subsequent registration of images from other modalities.

With respect to the last objective for image processing function, image registration is the process of determining the alignment between two images that have overlapping regions, where the images may be acquired at different times and/or by different sensors. The difficulty in aligning such images is further increased during multi-modal image registration, where the images are acquired using different imaging techniques (e.g., two images that share similar content may have very different intensity mappings).

For some embodiments, dynamic selection with respect to inputs means that one or more inputs can be selected or unselected in real time for routing to one or more image processing elements. For additional embodiments, dynamic and iterative selection with respect to processing elements means that a selected image stream can be routed to one or more image processing elements simultaneously and in real time. The routing may be based upon criteria relating to the image stream's source, the image stream's content, or on the processing results of a preceding image processing element. The output of an image processing element may be directed back to the system or method for routing to a subsequent image processing element, or to one or more image outputs that supply an image stream to an output device (e.g., display, image recorder, or other image processor, or transmission device).

The image stream interface for some embodiments may be configured to receive the image stream from an image stream capture device, an image stream playback device, a computer system, a sensor device (e.g., a medical device like an endoscope). The image stream output interface for some embodiments may be configured to output to a display (e.g., liquid crystal display monitor), a computer system, or recording device (e.g., digital video recorder). Further, in some embodiments, the system may be configured to output an image stream through a virtual display. One area where the alignment of images of different modalities (i.e., multi-modal image registration) is important is in the field of medical imaging. Different medical imaging techniques, such as x-rays, computed tomography (CT), magnetic resonance imaging (MRI), and positron emission tomography (PET), reveal different types of information about the body that can be used in the diagnosis of a disease. For example, consider the comparison of a slice from a cranial Tl-weighted MRI scan and its corresponding CT scan. The bone structure of the head, for example, will be clearly visible in the CT scan, and indicated by the bright areas in the image. The bone structure has a higher radio density than the surrounding tissue. This is not the case for an MRI scan where, unlike the CT scan, tissue differences can be clearly distinguished. Accordingly, the alignment of images of different modalities (e.g., image from a MRI scan and a CT scan) would allow for a better overall picture of a patient's condition.

Accordingly, in some embodiments, algorithms such as edge detection, sum of squared differences (SSD) and Fast Fourier Transform (FFT) are programmed into the image processing module such that multi-modal registration of images, such as from multiple medical imaging modalities, can be achieved. Sum of squared differences (SSD) is a common metric used for judging image similarity by a weighted sum of squared differences (SSD) cost function. The evaluation of the SSD cost function can be performed efficiently using the Fast Fourier Transform (FFT) to determine the optimal translation between two images based on pixel intensities.

In some embodiments, the image stream enhancement function performed by the image processing module comprises an auto-focus function capable of adjusting focus of an image stream capture device that is coupled to the image stream input interface and producing the image stream. For example, the auto-focus function may comprise the operations of: performing an edge detection algorithm on the image stream, thereby producing the processed image stream; and generating focus instructions for the image stream capture device based on the processed image stream. In further such embodiments, the operations of the auto-focus function are repeated iteratively until the image stream capture device is in-focus. In other embodiments, the edge enhancement algorithm utilizes a Laplacian convolution.

In certain embodiments, the system further comprises a control interface through which a user may operate or configure the system, among other things (e.g., check status of the system). For some such embodiments, the control interface may comprise a display touch panel having a graphical user interface, a keyboard, or a mouse, which are all examples of human machine interfaces (HMIs). For particular embodiments where the image stream output interface is outputting to a computer system, the control interface may be directly connected to the system and not connected to the computer system.

In some embodiments, the system can detect what type of image stream input interface, image stream output interface, or image processing module is present in the system, and configure the system according to the type. Further, in some embodiments, the system can detect what type of image stream input interface, image stream output interface, or image processing module is present in the system, and configure the control interface according to the type. For example, the system may detect the types of circuit cards present in each card slot of its chassis, self-configure the mix of image input cards, image processing cards, and image output cards detected, and present to the user a visual representation interface according to the mix for the purpose of providing image routing choices. It should be noted that in some embodiments the control interface comprises virtual buttons.

Various embodiments may enable multiple users/viewers to collaboratively control a system or method for switching multiple input image streams to multiple output devices, while providing optional image processing functions on the image streams. The collaborative control may, in real time, create, remove, reposition, or resize one or more virtual displays being outputted to an output device. Virtual displays may permit a collaborative user/viewer to split-screen, implement a picture-in-picture (PIP) window, and determine image stream source for a virtual display (e.g., to display new information). The collaborative control may allow multiple points of access, whereby multiple collaborative users/viewers can simultaneously access the collaborative control and dynamically update or reconfigure the virtual displays or the image stream being displayed in a virtual display.

The collaborative control interface may comprise a web-based interface that enables operation of the system, configuration of the system, or a status check of the system, and wherein the web-based interface is accessible by the users by way of a network connection with the system (e.g., Ethernet, Wi-Fi, or serial connection). The collaborative control interface may be further configured to receive commands from the users, store the commands into a queue, and perform the commands on the system in accordance with the queue. The commands may relate to operating the system, configuring the system, or checking a status of the system. The system may detect what type of image stream input interface, image stream output interface, or image processing module is present in the system, and configure the collaborative control interface according to the type.

Where at least one of the users is an administrative user and at least one of the users is a non-administrative user, a command from the administrative user through the collaborative control interface may be performed before a command from the non-administrative user. Where at least one of the users is an administrative user and at least one of the users is a non-administrative user, the administrative user may operate the system, configure the system, or check a status of the system through the collaborative control interface at the exclusion of the non-administrative user.

An exemplary method for collaboratively switching an image stream input to an image stream output, comprising: receiving a first command from a first user by way of a collaborative control interface accessible by two or more users simultaneously, wherein the first command relates to configuring a switching matrix in communication with a plurality of image stream input interfaces and an image stream output interface, and wherein the switching matrix is configured to selectively map an image stream input interface of the plurality of image stream input interfaces to the image stream output interface; and receiving a second command from a second user by way of the collaborative control interface, wherein the second command relates to configuring the switching matrix. The method may then store the first command and the second command (e.g., based on time of receipt, command type, user or user type issuing the command), in a queue; and perform the first command and the second command in accordance with the queue, thereby configuring the switching matrix in accordance with the first command and the second command. Subsequently, the method may receive an original image stream from the image stream input interface of the plurality of image stream input interfaces; and using the switching matrix (e.g., as configured by the first and second commands) to selectively map the original image stream to the image stream output interface.

In various embodiments, storing the first command and the second command in the queue may be based on an order in which the first command and the second command are received, based on a first priority of the first command and a second priority of the second command, or based on a first user type of the first user and a second user type of the second user.

Where the switching matrix outputs the original image stream to a virtual display, in a mapped image stream, being outputted to the image stream output interface, the first command or the second command may include creating the virtual display, closing the virtual display, resizing the virtual display, repositioning the virtual display within the mapped image stream being outputted to the image stream output interface, or moving the virtual display to another mapped image stream being outputted to another image stream output interface.

An exemplary system for switching control between a plurality of computer systems, comprising a plurality of image stream input interfaces, wherein a first image stream input interface of the plurality of image stream input interfaces is configured to couple with a first computer system of the plurality of computer systems, and wherein a second image stream input interface of the plurality of image stream input interfaces is configured to couple with a second computer system of the plurality of computer systems. The system may further comprise a plurality of computer input device interfaces (e.g., Universal Serial Bus [USB], PS/2, AT connector, Bluetooth, Infrared [IF], or FireWire), wherein a first computer input device interface of the general plurality of computer input device interfaces is configured to couple with the first computer system, and wherein a second computer input device interface of the plurality of general computer input device interfaces is configured to couple with the second computer system.

The system may additionally comprise: a central computer input device interface (e.g., Universal Serial Bus [USB], PS/2, AT connector, Bluetooth, Infrared [IF], or FireWire); a central image stream output interface; and a switching matrix in communication with the plurality of image stream input interfaces, the plurality of general computer input device interfaces, the central computer input device interface, and the central image stream output interface. The switching matrix may be configured to map the first image stream input interface to a first virtual display being outputted through the central image stream output interface and map the second image stream input interface to a second virtual display being outputted through the central image stream output interface. The switching matrix may be further configured to selectively map the central computer input device interface to the first computer input interface or the second computer input interface based on a location of an input cursor with respect to a first display region being outputted through the central image stream output interface or a second display region being outputted through the central image stream output interface. The first virtual display may be in the first display region, the second virtual display may be the second display region, and the input cursor may be controlled by way of the central computer input device interface.

Selectively mapping the central computer input device interface to the first computer input interface or the second computer input interface may be further based on whether the input cursor is entering or exiting the first display region or the second display region. In some embodiments, the first virtual display may coincide with the first display region, and the second virtual display may coincide with the second display region. Depending on the embodiment, the input cursor may be a mouse being controlled by a mouse coupled to the central computer input device interface or a keyboard cursor being controlled by a keyboard coupled to the central computer input device interface.

An exemplary method for switching control between a plurality of computer systems, comprising: receiving a first image stream at a first image stream input interface configured to couple with a first computer system of the plurality of computer systems; and receiving a second image stream at a second image stream input interface configured to couple with a second computer system of the plurality of computer systems. The method may further comprise: using a switching matrix to map the first image stream from the first image stream input interface to a first virtual display being outputted through a central image stream output interface; and using the switching matrix to map the second image stream from the second image stream input interface to a second virtual display being outputted through the central image stream output interface. The method may additionally comprise receiving input information from a central computer input device interface; and using the switching matrix to selectively map the control information from the central computer input device interface to a first computer input device interface or a second computer input device interface based on a location of an input cursor with respect to a first display region or a second display region. The first display region may be outputted through the central image stream output interface, and the second display region may be outputted through the central image stream output interface. The first computer input device interface may be configured to couple with the first computer system, and the second computer input device interface may be configured to couple with the second computer system. The first virtual display may be in the first display region, the second virtual display may be the second display region, and the input cursor may be controlled by way of the central computer input device interface.

Other embodiments provide for a computer readable storage medium having instructions embedded thereon to cause a processor to perform operations similar to those described above with respect to the various systems and methods in accordance with the present invention.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

DETAILED DESCRIPTION OF THE PREFERRED EMBODIMENT

Figure 1:
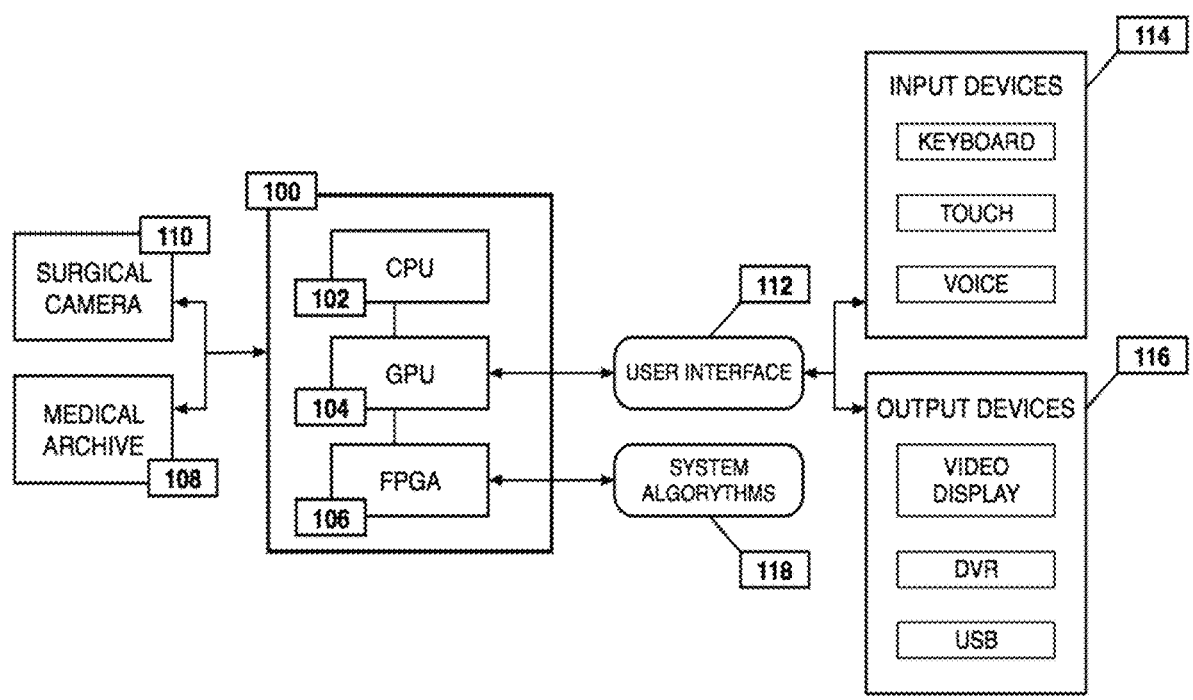
FIG. 1 is a block diagram illustrating an example of the overall processing system that may be used in implementing various features of embodiments of the disclosed technology.

FIG. 1 is a block diagram illustrating an example of the overall processing system that may be used in implementing various features of embodiments of the disclosed technology. In accordance with the preferred embodiment of the present invention, the processing system 100 consists of processor elements such as: a central processing unit (CPU) 102; a graphics processing unit (GPU) 104; and a field programmable gate array (FPGA) 106. The processing system 100 may be used to retrieve and process raw data derived from a surgical camera 110 or a data storage device, such as a medical archive 108. The surgical camera 110 or medical archive 108 transmits a data stream to the processing system 100, whereby that data is processed by the CPU 102. The FPGA 106, connected to the CPU 102 and the GPU 104, simultaneously processes the received data by using a series of programmed system algorithms 118, thus functioning as an image clarifier within the processing system 100. The GPU 104 communicates with the user interface 112 to display the received data from the medical archive 108. The GPU 104 enables the user interface to then communicate the data to connected input devices 114 and output devices 116. The user interface 112 can communicate to multiple input 114 and output devices 116 simultaneously. An input device 114 can include, for example, a keyboard, touchscreen or voice activated device. An output device 116 can include, for example, a video display, a digital video recorder (DVR) or universal serial bus (USB).

Figure 2:
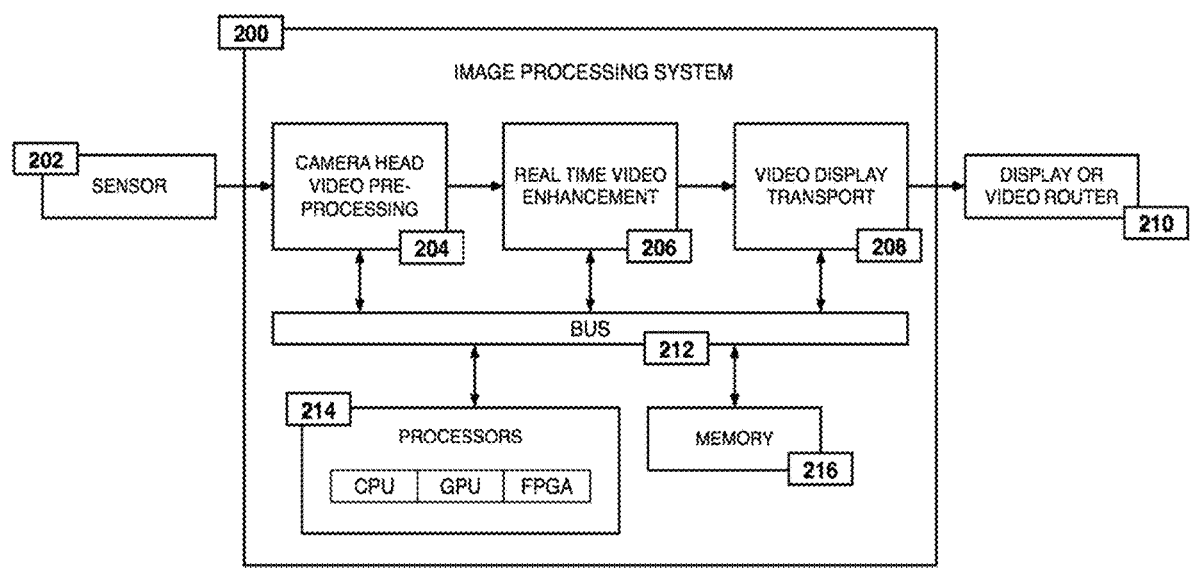
FIG. 2 is a block diagram illustrating an example of the image processing system that may be used in implementing various features of embodiments of the disclosed technology.

FIG. 2 is a block diagram illustrating an example of the image processing system that may be used in implementing various features of embodiments of the disclosed technology. In accordance with the preferred embodiment of the present invention, the image processing system 200 consists of three components that process image data received from a sensor 202 in order to send that data to a display or video router 210. The three components of the image processing system 200 are: camera head video pre-processing 204; real time video enhancement 206; and the video display transport 208 function. Image data is collected by a sensor imaging device 202, and is then transmitted to the camera head video pre-processing component 204 within the image processing system 200. This data may be, for example, a raw video image that is pre-processed using various image processing algorithms. Image pre-processing may also include software modules for image registration and segmentation to optimize the video data and communicate via the system bus 212 with the internal system processors 214: the CPU; GPU; and FPGA.

The pre-processed image data is transmitted to the real-time video enhancement 206 component, whereby the image data is enhanced to improve clarity or highlight certain details. Once the image data resolution has been enhanced, the video display transport 208 component completes image post-processing, formatting from the initial sensor resolution to the eventual display resolution, for example, enhancing the video data to 1080p HD or 4K display resolution or using software modules such as video cross conversion, scaling and adding graphic overlays. The processed image data is then transmitted from the image processing system 200 to the display or video router 210. The video display transport also saves the processed image data to the processing system memory 216 that can consist of internal and external memory storage.

Figure 3:
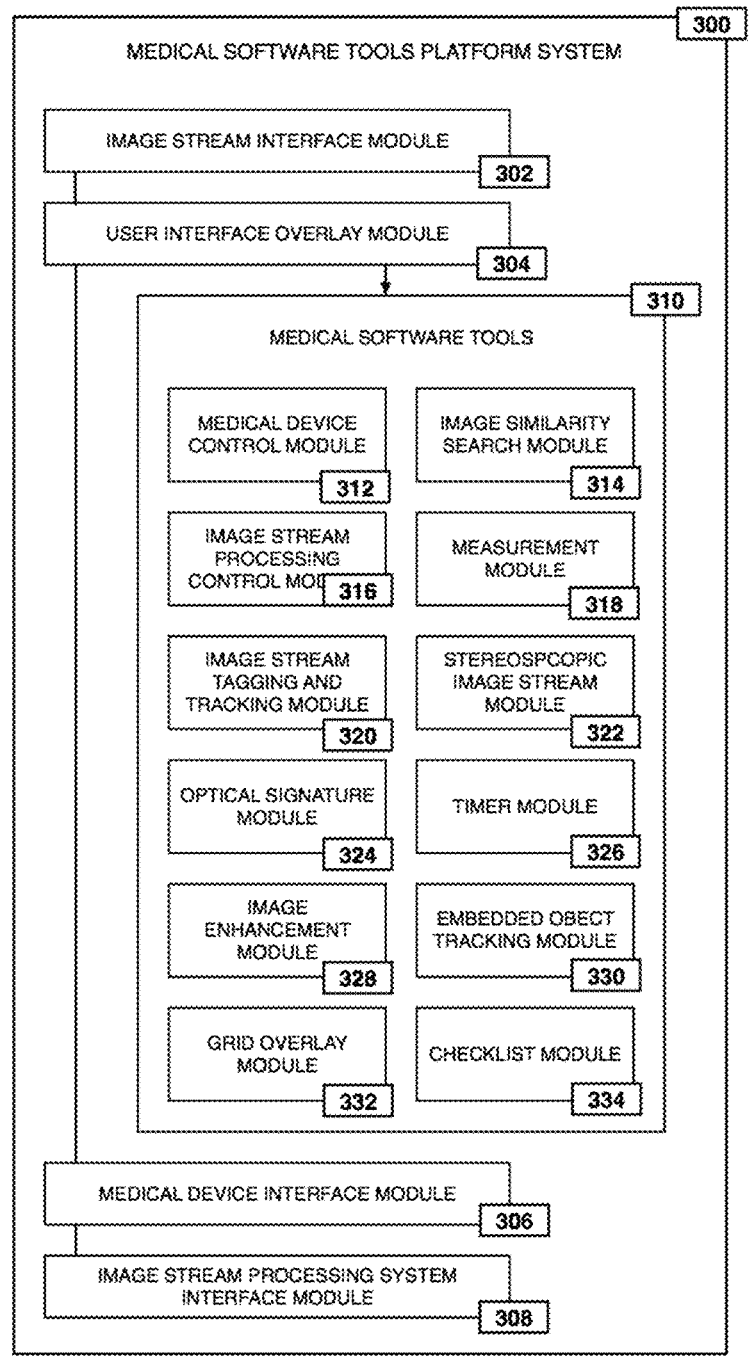
FIG. 3 is a block diagram illustrating an example medical software tools platform in accordance with some embodiments of the technology described herein.

FIG. 3 is a block diagram illustrating an example medical software tools platform system in accordance with some embodiments of the technology described herein. The medical software tools platform provides access to medically-oriented applications (apps) or widgets that can assist members of the surgical team during an operation. For example, during a surgery it is common to clamp a blood vessel for a short period, but the clamp must be removed before damage occurs to the tissue that depends on the vessel's blood flow for necessary oxygenation. A timer app could be used to apprise the surgeon of the elapsed time and also the remaining time that it is safe for the clamp to be in place. Additionally, the timer app could monitor the area around the clamped blood vessel for changes in color which would indicate declining levels of tissue oxygenation and generate an alert when the color indicates tissue oxygen saturation may be declining below safe levels. In a second example, a grid overlay app could overlay gridlines over a portion of the displayed video stream. The gridlines provide a means of marking the location of biopsy samples. Additionally, the gridlines allow the surgeon to accurately measure anatomical structures that are displayed. As a third example, an annotation tool app allows the surgeon to superimpose circles or squares or to draw around features or areas of interest displayed on the screen and associate digital tags or notes for future reference. In a final example, when surgeons excise diseased tissue it is common to also remove a narrow margin around it. The challenge, of course, is to clearly visualize and identify the demarcation between diseased and healthy tissue. A boundary tool app could identify anomalous areas of tissue using texture analysis techniques to assist the surgeon in finding diseased areas and demarcating them. Such a tool could potentially also be useful in helping a surgeon identify the best locations for obtaining biopsy samples.

In accordance with the preferred embodiment of the present invention, the medical software tools platform system 300 includes: an image stream interface module 302; a user interface overlay module 304; medical software tools 310; a medical device interface module 306; and an image stream processing system interface module 308. The medical software tools platform system 300 may be integrated, in whole or in part, into a video display or an image stream processing system utilized in an operating room. The image stream interface module 302 may receive an image stream acquired by a surgical camera or the like. Depending on the embodiment, the image stream may be received directly from the surgical camera, or may be provided by way of one or more components, such as an image stream processing system. The image stream received from the image stream interface module 302 may vary in resolution, frame rate, format, and protocol according to the surgical camera or the image stream processing system providing the image stream.

The user interface overlay module 304 may provide a user interface to the medical software tools platform system 300, which may include one or more graphical user interface (GUI) elements presented over the image stream received through the image stream interface module 302. For some embodiments, the user interface comprises a bottom toolbar configured to be presented over the image stream, and configured to provide access to various medical software tools 310 available through the medical software tools platform system 300.

The medical software tools 300 may include one or more medical software tools, such as medically-oriented applications or widgets, which can be utilized with respect to the image stream being received through the image stream interface module 302. The medical software tools 310 platform includes but is not limited to: a medical device control module 312; an image similarity search module 314; an image stream processing control module 316; a measurement module 318; an image stream tagging and tracking module 320; a stereoscopic image stream module 322; an optical signature module 324; a timer module 326; an image enhancement module 328; an embedded object tracking module 330; a grid overlay module 332; and a checklist module 334.

The medical device interface module 306 may facilitate communication between the medical software tools platform system 300, one or more of the medical software tools 310, and one or more various medical devices utilized in an operating room. The image stream processing system interface module 308 may facilitate communication between the medical software tools platform system 300 and an image stream processing system utilized to process an image stream acquired by a surgical camera or the like. Through the communication, the image stream processing system interface module 308 may transmit control data to an image stream processing system, or receive an image stream from a surgical camera as processed by the image stream processing system. The image stream processing system interface module 308 may include various data interfaces, including wired or wireless network interfaces and serial communication interfaces.

Figure 4:
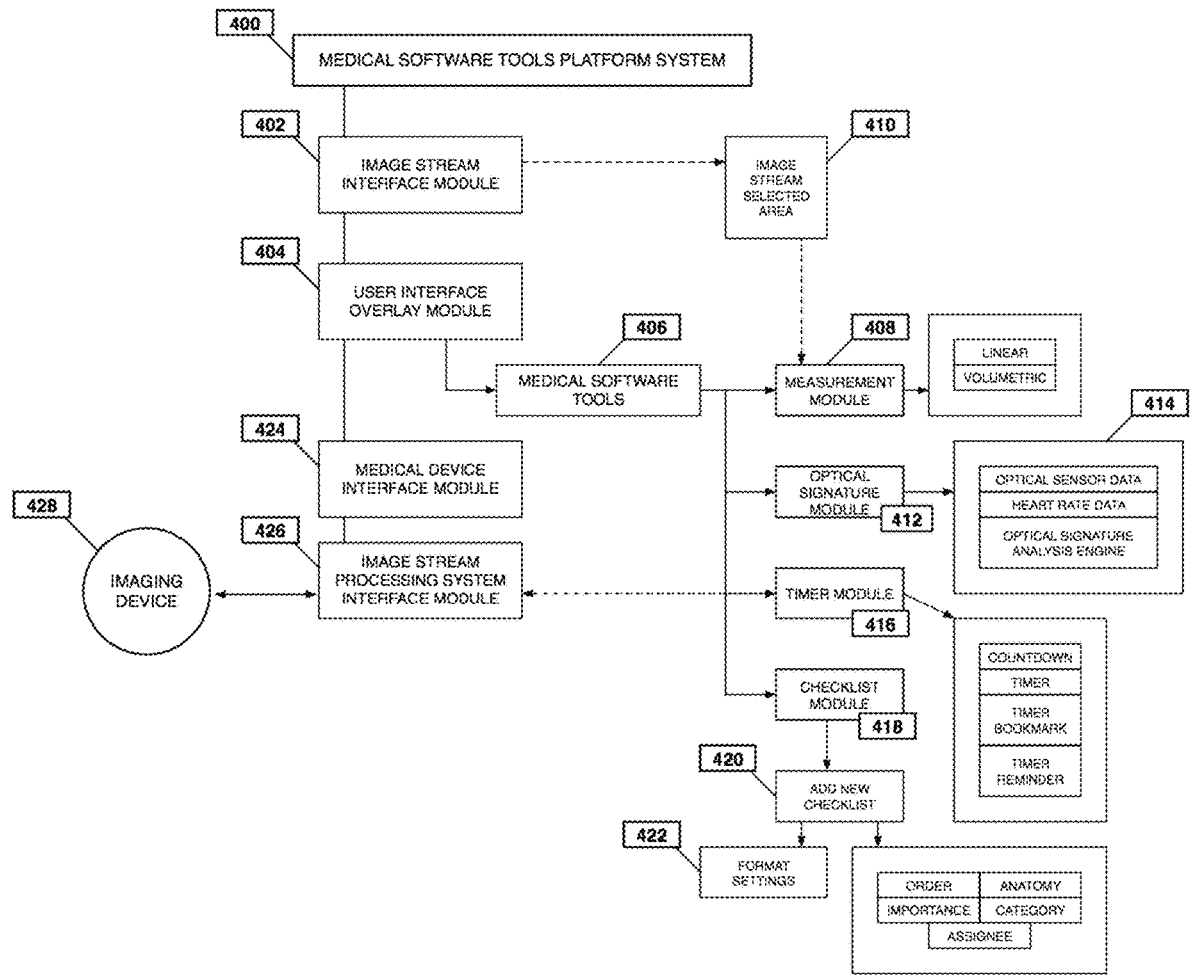
FIG. 4 is a block diagram illustrating the measurement, optical signature module, timer and checklist modules within the medical software tools platform.

FIG. 4 is a block diagram illustrating the measurement, optical signature module, timer and checklist modules within the medical software tools platform. In accordance with the preferred embodiment of the present invention, the medical software tools platform system 400 may receive an image stream from an image stream processing system through the image stream interface module 402. A specific area of the overall image stream can be selected 410 and utilized within the user interface overlay module 404, which may include one or more graphical user interface (GUI) elements presented over the image stream received through the image stream interface module 402. the user interface overlay module 404 enables communication between the medical software tools platform system 400, and one or more of the medical software tools 406, such as the measurement module 408, the optical signature module 412, timer module 416, and checklist module 418.

The medical device interface module 424 may facilitate communication between the medical software tools platform system 400, and one or more of the medical software tools 406, such as the measurement module 408, optical signature module 412, timer module 416, and checklist module 418. The measurement module 408 may facilitate measurement of one or more anatomical structures or tissue presented in the content of an image stream received through the image stream interface module 402. Depending on the embodiment, the measurement module 408 may enable a user (e.g., surgeon) to select a region 410 in the image stream and determine a measurement based on the selected region. The measurement may include linear measurements (e.g., width, height, length) and volumetric measurements of an anatomical structure or tissue delineated by the selected region.

The optical signature module 412 may facilitate the processing of signature data 414 such as optical sensor data, heart rate data and the optical signature analysis engine. The timer module 416 may facilitate the addition of one or more countdown timers, clocks, stop-watches, alarms, or the like, that can be added and displayed over the image stream through the user interface provided by the user inter face overlay module 404. For example, the timer module may allow a user (e.g., surgeon) to add a countdown timer in association with a surgical step (e.g., clamping an artery). For example, a countdown timer may be associated with a specific blood vessel that must be temporarily clamped during surgery but must be opened within a small window of time. A user may be able to select from a list of pre-defined countdown timers, which may have been pre-defined by the user. A clock when added may be used as a time bookmark during surgical procedures. The timer module 416 may communicate with an image stream processing system interface module 426 utilized in an operating room to process an image stream acquired by an imaging device 428.

The checklist module 418 may enable a user (e.g., surgeon) to add and maintain a checklist in connection with a medical procedure 420. For example, the checklist module 418 may provide a list of checklist items for a medical procedure. Each checklist item may indicate whether a step of the medical procedure has been completed or has yet to be completed. The checklist module 418 may allow a user to present the checklist in different ways using the checklist module formatting settings 422. For instance, the checklist items may be organized and presented according to their procedural order, their importance, their relation to a patient's anatomy, their category, or their assigned individual (e.g., checklist item is the nurse's responsibility versus the surgeon's responsibility). In another example, the checklist items may be presented in using different visual structures, such as a tree structure or a scrolling list.

Figure 5:
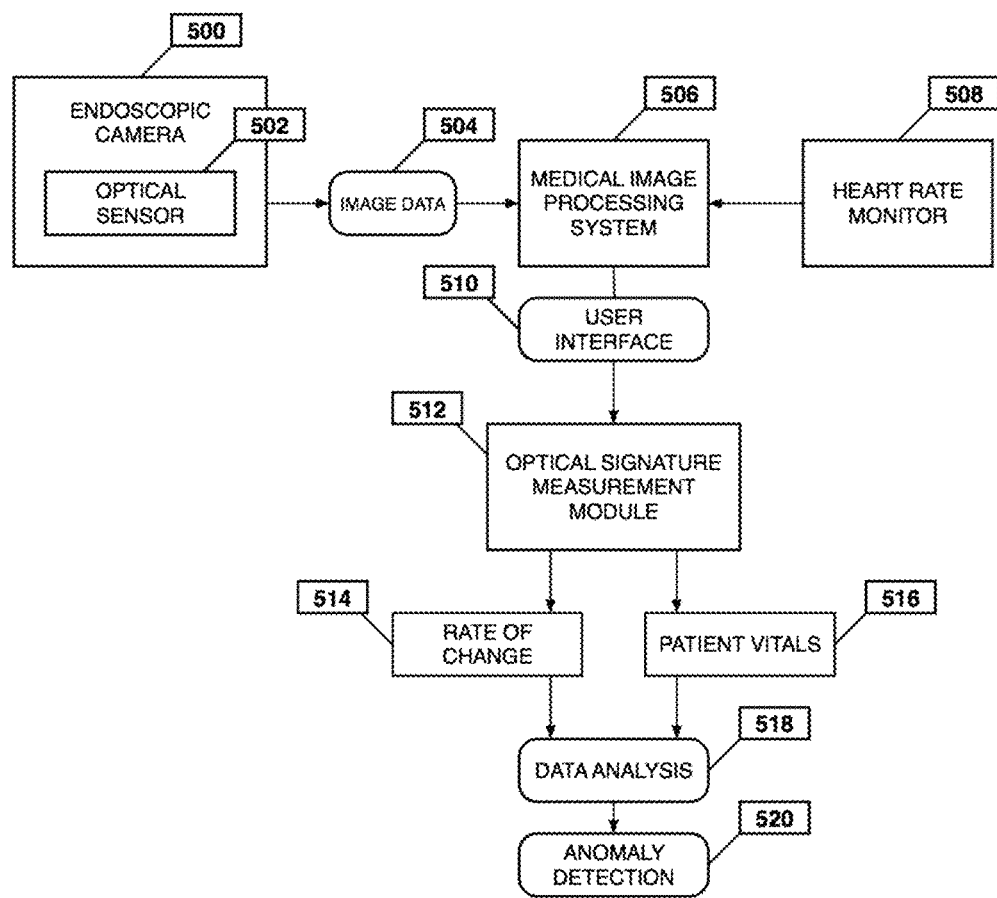
FIG. 5 is a block diagram illustrating the optical signature measurement module within the medical software tools platform.

FIG. 5 is a block diagram illustrating the optical signature measurement module 512 within the medical software tools platform. In accordance with the preferred embodiment of the present invention, an optical sensor 502 located within an endoscopic camera lens 500 registers the momentary change in the spectral characteristics (or components) reflected from a tissue surface. This image data 504 is transmitted to the medical image processing system 506, which can also receive data from a device such as a patient heart rate monitor 508. The medical image processing system 506 processes and transmits the image data 504 from the optical sensor with data from the heart rate monitoring device 508 to the user interface 510, whereby all sets of data are received through the optical signature measurement module 512, displaying the rate of change 514 in the optical signature simultaneously with the patient vitals data 516. This data is analyzed 518 in the module and the results of any anomaly detection 520 are displayed to the user. The slight changes in one of more of the spectral components, and the speed at which they change, in relation to a source stimulus (heartbeat, breath, external stimulus) indicates the arrival of blood, contrast agents, or oxygen absorption. Combinations of the components can be used to characterize different types and states of disease and to identify the margins of tumors and diseased areas. In addition to spectral components, changes in temperature and its speed of change can be measured to similarly characterize surface and sub-surface anomalies.

Figure 6:
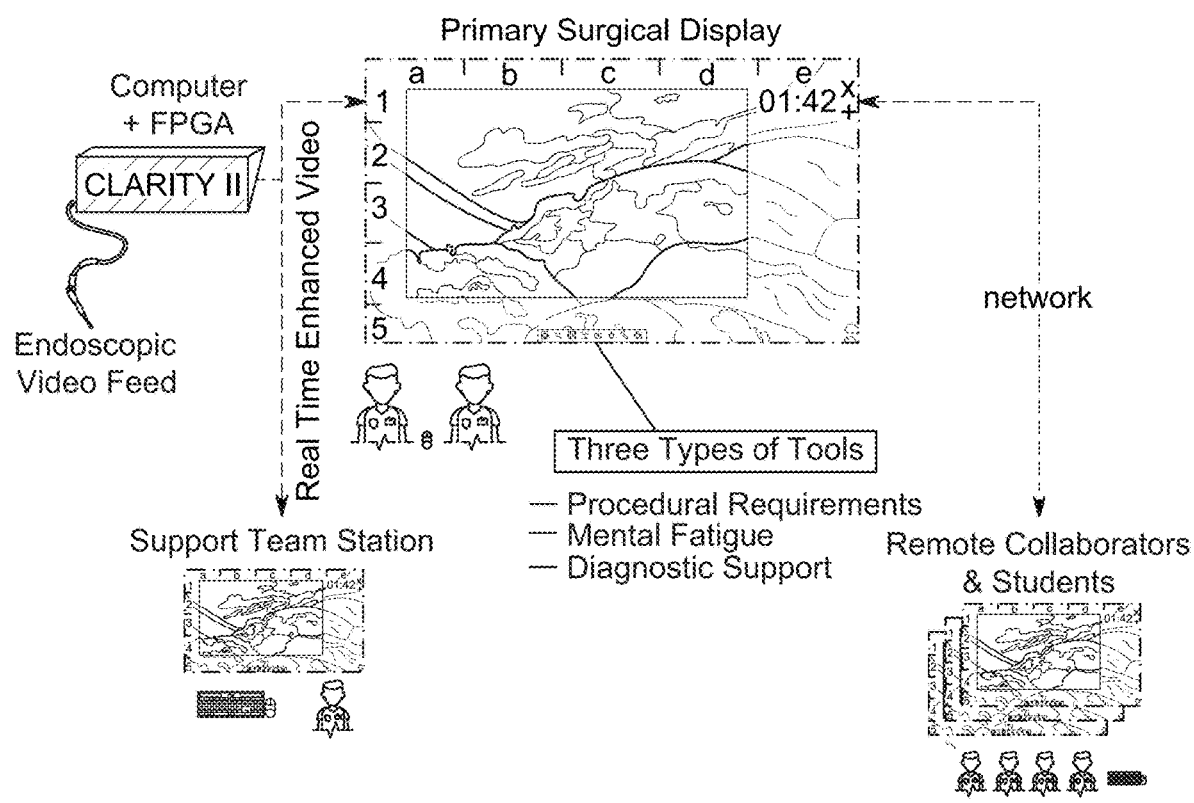
FIG. 6 is a rendering of the Surgeon's Desktop software toolset

FIG. 6 is a rendering of the Surgeon's Desktop software toolset. In accordance with the preferred embodiment of the present invention, the Surgeons Desktop provides a framework for providing software apps or widgets on a surgical display that can aid surgeons in performing various tasks during surgeries. The tools can assist a surgeon, for example, with procedural requirements, such as checklists for specific surgical steps; or ease mental fatigue, for example applying enhanced or augmented imagery making it easier to see an area of interest; or provide diagnostic support, such as identifying and highlighting suspicious areas of tissue.

A new tool pertaining to tissue analysis is presented herein. Specifically, the tool measures change in color intensity and the rate at which it changes in response to: a) heart-beat pushing blood, b) breathing pushing oxygen, c) light from a light source. Furthermore, some light frequencies can cause tissue temperature to rise, which can create a change in pressure which can be measured which is called a "photoacoustic" response.

In addition, some of the Surgeon Desktop tools incorporate algorithmic-based image processing to improve visibility during endoscopic or laparoscopic procedures. For best results, the algorithms need to be adjusted for the particular subject matter and also the individual preferences of the surgeon. Therefore, the specific mathematical operations within an individual algorithm and the specific combinations of algorithms that are applied are typically determined through a lengthy process of trial and error. Described herein is a new algorithm developer tool that enables developers or advanced users to rapidly explore the operation of various image processing algorithms and various combination of algorithms to obtain the best image clarity.

Figure 7:
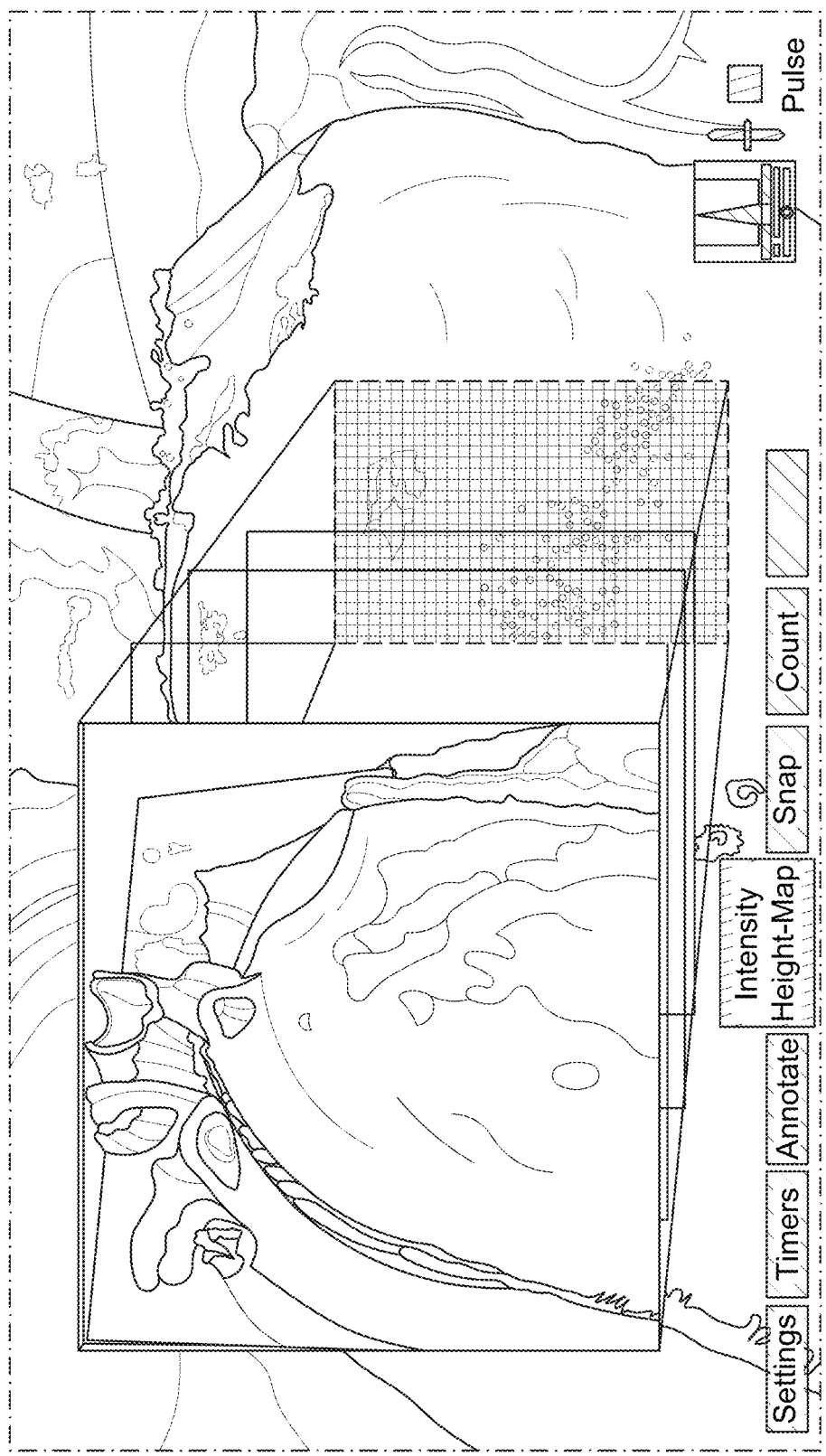
FIG. 7 is a rendering of the intensity height map tissue analysis tool

FIG. 7 is a rendering of the intensity height map tissue analysis tool. In accordance with the preferred embodiment of the present invention, a method for detection of tumor margins by comparing previous readings, such as a spectral signature, was described in a prior filing. The present invention identifies tumor margins in real time by comparing changes and rates of change in a diseased area to adjacent and nearby surrounding areas. Areas are defined by finding groups that have similar spectral signatures or rates of change. In certain embodiments, an area of interest is first analyzed to identity those portions of the tissue that respond to an influx of blood or body fluid corresponding to or in synchronization with the patient's heartbeat and only those portions are included in the comparison. In a preferred embodiment, the changes and rates of changes can be analyzed using artificial intelligence that utilizes a database of historical samples.

The tissue analysis tool includes the following three sub-functions that allow a surgeon to obtain different views to reveal greater detail or monitor an area of interest. The three functions are height map, which measure pixel intensity; color map, which applies different color schemes; and margin guide, which provide a freeform drawing tool that can be used to highlight and geo-position an area interest. To use the height map, the user selects the tool from the on-screen tool bar and sweeps an area of interest with the mouse. The selected area is enlarged and rendered as a "Picture-In-Picture" insert. The insert simulates a 3D view by mapping the area's pixels onto an elevation grid using the pixel intensities to create a "height-map". The user can experiment with different views and degrees of detail by rotating the insert in 3D using a mouse, adjusting for more or less detail with the window/level sliders, and by scaling up/down with the vertical bar or mouse wheel. The "Pulse" button animates the pixel heights in relation to the intensity change resulting from the pulse of pumping blood into the local vascular network ("Pixels dance to the tune of the heartbeat"). The rise and fall height and rate of change in pixel intensity demonstrate the different responses of diseased and healthy tissue.

Figure 8:
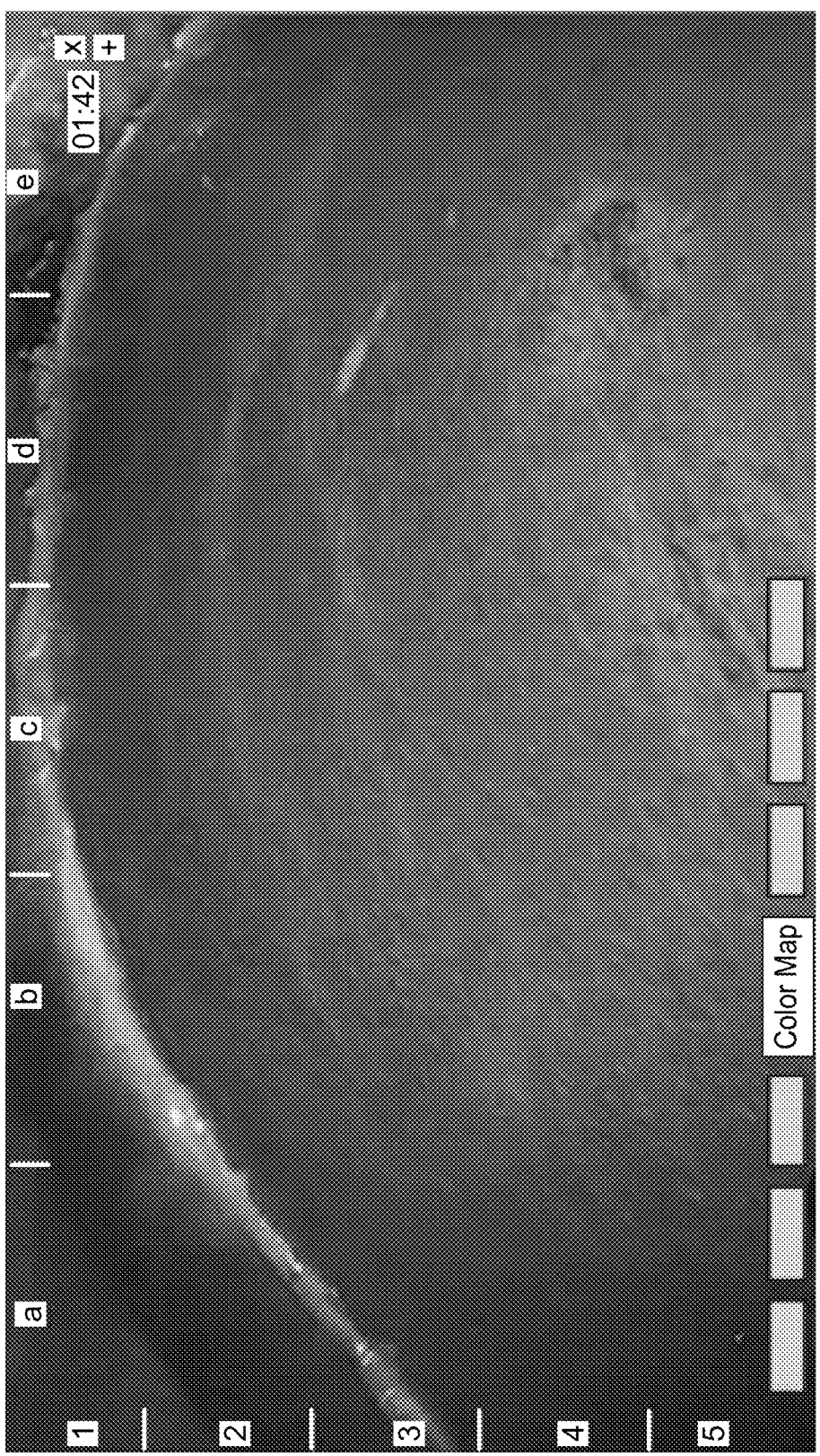
FIG. 8 is a rendering of the color map tool.

FIG. 8 is a rendering of the color map tool. In accordance with the preferred embodiment of the present invention, the Color Map tool presents the surgeon with a choice of views of the tissue surface with a choice of color maps. The goal is to more clearly characterize the margins of diseased tissue. In one embodiment, the color map tool can be used to temporarily counteract or undo the visual effects of a fluorescent contrast agent. In certain situations, a surgeon may prefer more natural coloring and contrast which may make it easier to see certain details.

Figure 9:
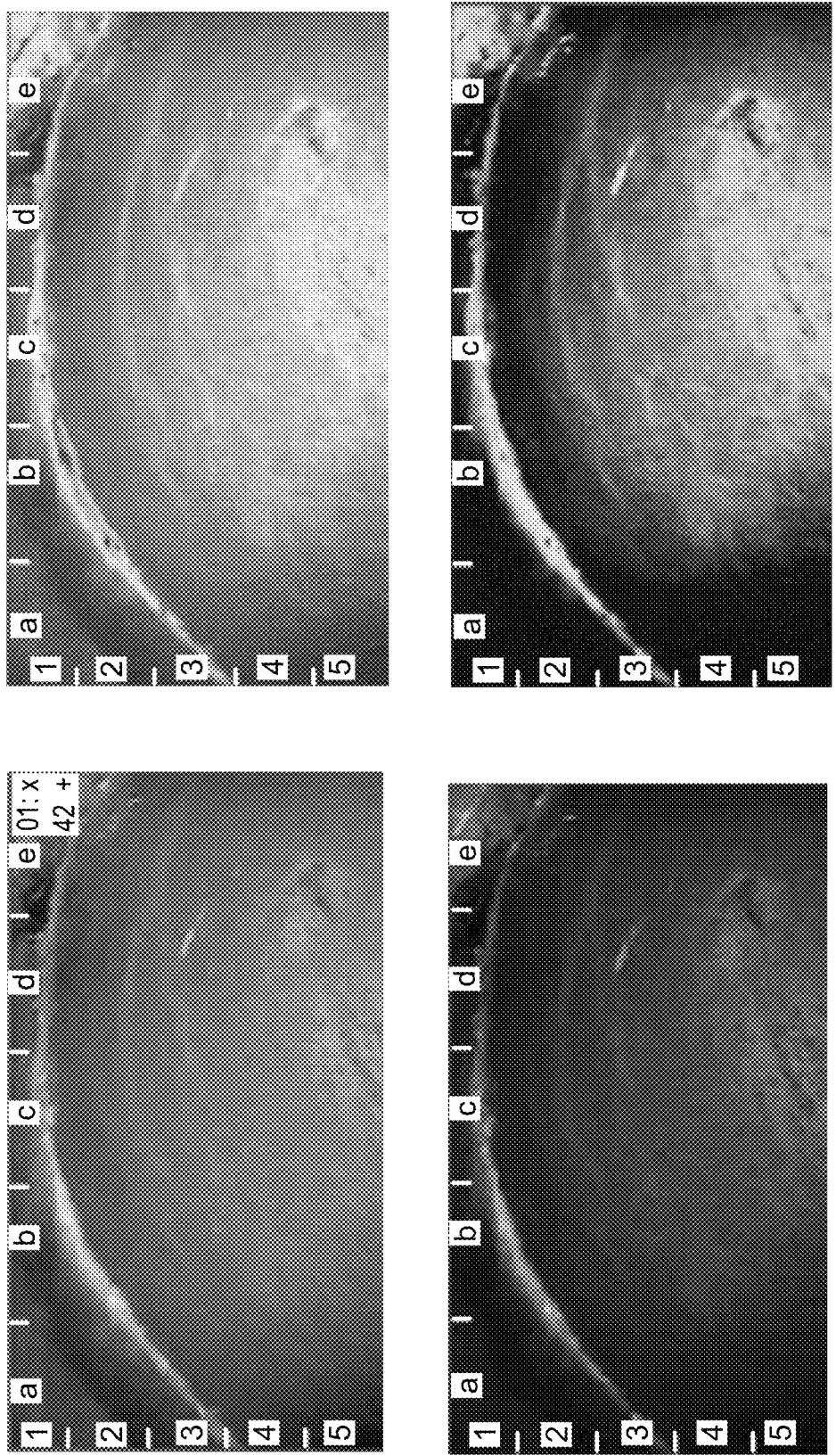
FIG. 9 is a rendering of the various color display tables for the color map tool.

FIG. 9 is a rendering of the various color display tables for the color map tool. In accordance with the preferred embodiment of the present invention, there are main menu settings that personalize the default choices for each surgeon. The defaults include the presentation format and color translation tables to display when the Color Map icon is selected. Mouse clicking a selection brings it to the primary display window where it is subject to other tools for further analysis.

Figure 10:
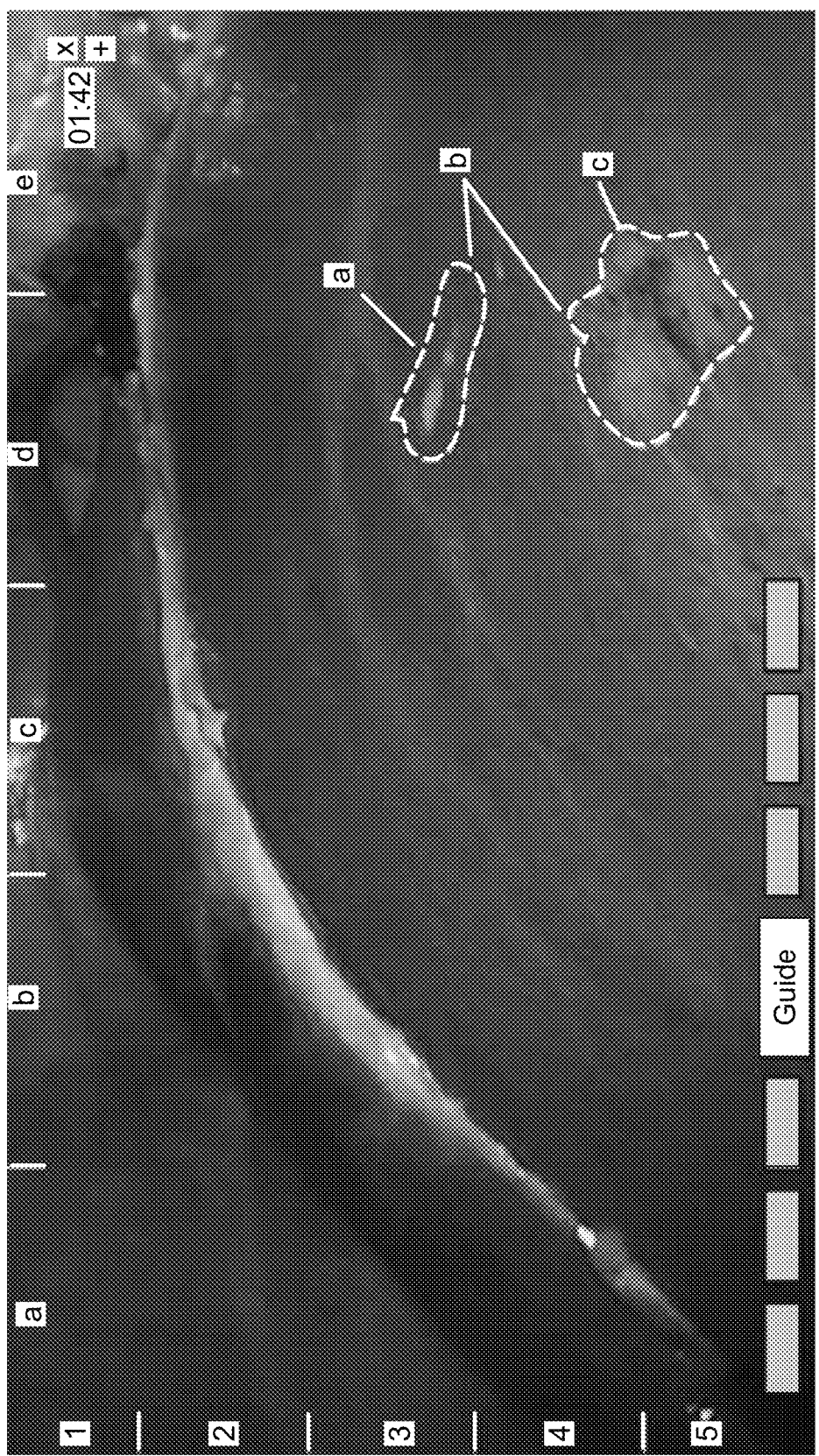
FIG. 10 is a rendering of the margin guide outline tool.

FIG. 10 is a rendering of the margin guide outline tool. In accordance with the preferred embodiment of the present invention, the Margin Guide tool provides the surgeon with a freeform drawing tool to outline an anomalous area on the surface of tissue. The boundary line will stay anchored to its position as the underlying tissue moves. The anchoring points are identifiable features outside an enclosed boundary area. In the illustration, the "a, b, c" markers are unique identifiable tissue structures that are used to geo-position the margin outlines. The goal is to provide a persistent guide during an excision of a mass. The Margin Guide tool can also draw a suggested outline using the pixel intensities of surrounding tissue. A surgeon can then "fine tune" the shape as needed.

Figure 11:
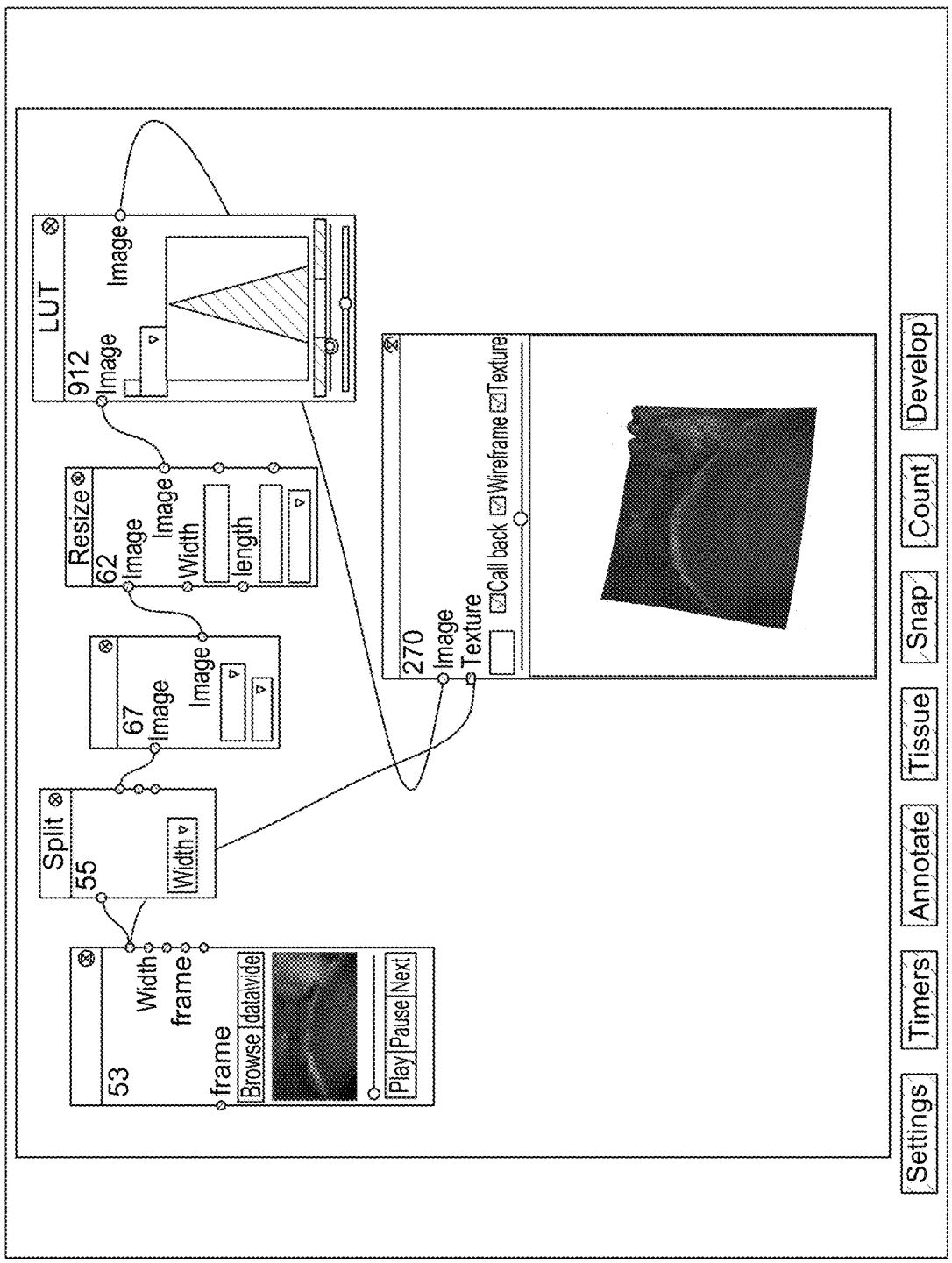
FIG. 11 is a rendering of the algorithm developer tool.

FIG. 11 is a rendering of the algorithm developer tool. In accordance with the preferred embodiment of the present invention, a graphical tool enables advanced users to test and create new algorithms. Video processing algorithms are a sequence of step-by-step mathematical operations that operate on an image flow in real time. The end result exposes and highlights features in the image not discernable by the human eye. The development cycle for a new algorithm requires iterative trial and error experiments and can be prohibitively time consuming. The Algorithm Developer tool enables an advanced user to flow the video through a sequenced series of mathematical functions (sub algorithms) selected from an extensible library of functions and view the result in near real time. Each new algorithm can be saved in the library and becomes instantly available for use as a high-level video processing function, or saved in the library to serve as a sub-algorithm for new development.

The example illustrates building a 3D "Height-Map" of pixel intensities to show variations on the surface of live tissue. The video is flowed through a sequence of five processing nodes selected by the algorithm developer. The output of each node becomes the input of the next node to create a new algorithmic function. The five-step sequence illustrated is: 1) "Video" node decodes recorded MPEG video and flows the frames to its output. The video node outputs a sequence of frames consisting of an array of RGB pixels, 2) "Split" node converts RGB color to YCbCr to acquire the luminance "Y" channel to get the intensity of each pixel, 3) "Imgproc" Image Processing node applies a Gaussian convolution filter to eliminate noise and smooth the image, 4) "Resize" node scales the image to a grid size suitable for mapping the elevation of pixel intensities, 5) "LUT" Look Up Table provides a slider to select a pixel range to expose more detail. The library of algorithmic functions includes a mix of both proprietary and open source modules from the public OpenCV archive.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that may be included in the disclosed technology. The disclosed technology is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the technology disclosed herein. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

What is claimed is:

1. A system for medical software tools, comprising:
    a data bus in communication with a processing device to transmit an image stream from a camera disposed in a medical device to an image stream processing interface module; and
    wherein said data bus conducts image post-processing and formatting of said image stream to match a display resolution of a user interface module;
    an optical sensor corresponding with said camera disposed in said medical device for registering changes in spectral characteristics reflected from an anatomical tissue surface under inspection;
    a data storage unit housed in said processing device to upload said image stream on to a medical archive over said user interface module;
    a user video enhancement component on said user interface module to render an graphic overlay over said image stream;
    a medical software tools component on said user interface module, configured to said processing device to provide a plurality of medical software tools through said user interface module;
    an optical signature module for said optical sensor utilizing an algorithmic-based image processing system to monitor said changes in said spectral characteristics of a diseased area and proximal areas of said anatomical tissue surface; and wherein said plurality of medical software tools are selected and customized by a medical professional to execute an operation with respect to said graphic overlay over said image stream.

2. The system of claim 1, further comprising of said optical signature module processing a change in color intensity and b. rates at which said color intensity changes in response to heartbeat pushed blood, breathing pushed oxygen and light intensity or modulation from a light source.

3. The system of claim 1, wherein said medical software tools utilizes a database of historical samples on said medical archive and uses said algorithmic-based image processing system to compare a rate of said changes in said spectral characteristics.

4. The system of claim 3, further comprising of said algorithmic-based image processing system utilizing a height map to measure pixel intensity, a color map to apply different color schemes, and a margin guide to provide a freeform drawing tool that can be used to highlight and geo-position an area interest.

5. The system of claim 3, further comprising of said algorithmic-based image processing system presenting an on-screen tool bar to enable a user to sweep an area of interest on said user interface module with a mouse.

6. The system of claim 4, wherein said medical professional can insert a 3D rendition from said height map using a mouse and adjust an image view to present more or less detail with a window, level slider, vertical bar, and mouse wheel.

7. A method for using medical software tools in a surgical environment, the method comprising of:
receiving an image stream of an anatomical structure from a camera disposed in a medical device;
enhancing said image stream in a first image stream processing system and formatting said image stream to a display resolution of a processing device with a data bus in communication with said processing device for video display transport;
transmitting said image stream over said first image stream processing system to a second image stream processing system;
uploading and storing said image stream on to a data storage unit within said processing device to generate a medical archive in a user interface module in said second image stream processing system;
registering changes in spectral characteristics reflected from tissue surface of said anatomical structure that is under inspection using an optical sensor corresponding with said camera disposed in said medical device;
rendering a graphic overlay over said image stream through a video enhancement component on said user interface module;
presenting a plurality of medical software tools on a medical software tools component on said user interface module;
analyzing, using an optical signature module for said optical sensor utilizing an algorithmic-based image processing system, said changes in said spectral characteristics of a diseased area and a proximal area of said anatomical structure; and
selecting said plurality of medical software tools to enable an execution of an operation with respect to said graphic overlay over said image stream deriving from said camera disposed in said medical device.

8. The method of claim 7, further comprising of the optical signature module processing a change in color intensity and b. rates at which the color intensity changes in response to heartbeat pushed blood, breathing pushed oxygen and light intensity or modulation from a light source.

9. The method of claim 7, wherein said medical software tools utilizes a database of historical samples on said medical archive and uses said algorithmic-based image processing system to compare a rate of said changes in said spectral characteristics.

10. The method of claim 9, further comprising of said algorithmic-based image processing system utilizing a height map to measure pixel intensity, a color map to apply different color schemes, and a margin guide to provide a freeform drawing tool that can be used to highlight and geo-position an area interest.

11. The method of claim 9, further comprising of the algorithmic-based image processing system utilizing a height map to measure pixel intensity, a color map to apply different color schemes, and a margin guide to provide a freeform drawing tool that can be used to highlight and geo-position an area interest.

12. The method of claim 10, wherein a medical professional can insert a 3D rendition from said height map using a mouse and adjust an image view to present more or less detail with a window, level slider, vertical bar, and mouse wheel.

13. The method of claim 7, wherein said medical archive stores processed image data to external memory storage in addition to said data storage unit within said processing device.

14. A system for registering changes in optical signatures using a suite of medical software tools, comprising:
a data bus in communication with a processing device to transmit an image stream from a camera disposed in a medical device to a first image stream processing system, and wherein said data bus conducts image post-processing and formatting of said image stream to match a display resolution of a user interface module on a second image stream processing system;
an optical sensor corresponding with said camera disposed in said medical device for registering changes in spectral characteristics reflected from an anatomical tissue surface under inspection;
said optical sensor configured with an optical signature module to monitor said changes in said spectral characteristics of a diseased area and proximal areas of said anatomical tissue surface, including a. said changes in color intensity and b. rates at which said color intensity alters in response to heartbeat pushed blood, breathing pushed oxygen and light intensity or modulation from a light source;
a data storage unit housed in said processing device to upload said image stream on to a medical archive over said user interface module, and wherein said medical archive stores historical samples of said anatomical tissue surface and uses an algorithmic-based image processing system to compare a rate of said changes in said spectral characteristics,
wherein said algorithmic-based image processing system is capable of executing a direction to measure pixel intensity, apply a color map to different color schemes of said anatomical tissue surface and said image stream;
a user video enhancement component on said user interface module to render an graphic overlay over said image stream;

a medical software tools component on said user interface module, configured to said processing device to provide a plurality of medical software tools through said user interface module; and wherein said plurality of medical software tools are selected and customized by a medical professional to execute an operation with respect to said graphic overlay over said image stream using a mouse and vertical bar presented on said user interface module.

15. The system of claim 14, wherein said algorithmic-based image processing system provides a margin guide that enables a freeform drawing tool for said medical professional to highlight and geo-position an area interest.

16. The system according to claim 14, wherein said user video enhancement component uses a graphical user interface to transmit said image stream.

17. The system according to claim 14, wherein a switching matrix communicates with said first image stream processing system and said second image stream processing system to manage display inputs and outputs of said image stream on said user interface module.

18. The system according to claim 16, wherein said user video enhancement component generates, by way of said processing device, an active timer for each frame of said image stream and an embedded object tracking module.

19. The system according to claim 18, wherein said active timer can be configured as a pre-defined countdown timer to monitor and control a duration of a surgical operation.

* * * * *